US005856163A

United States Patent [19]

Hashida et al.

[11] Patent Number: 5,856,163

[45] Date of Patent: Jan. 5, 1999

[54] LIPASES FROM HYPHOZYMA

[75] Inventors: Miyoko Hashida, Chiba; Masanobu Abo, Funabashi; Yukiko Takamura, Chiba, all of Japan; Ole Kirk, Copenhagen N., Denmark; Torben Halkier, Frederiksberg, Denmark; Sven Pedersen, Gentofte, Denmark; Shamkant Anant Patkar, Lyngby, Denmark; Mogens Trier Hansen, Lynge, Denmark

[73] Assignee: Novo Nordisk A/S, Bagsvaerd, Denmark

[21] Appl. No.: 347,335

[22] PCT Filed: Jun. 3, 1993

[86] PCT No.: PCT/DK93/00194

§ 371 Date: Dec. 22, 1994

§ 102(e) Date: Dec. 22, 1994

[87] PCT Pub. No.: WO93/24619

PCT Pub. Date: Dec. 9, 1993

[30] Foreign Application Priority Data

Jun. 3, 1992 [DK] Denmark .................................. 735/92

[51] Int. Cl.[6] ................................ C12N 9/20; D21C 3/00

[52] U.S. Cl. ............................................ 435/198; 435/278

[58] Field of Search ................................ 435/198, 172.1, 435/278, 174, 176, 177, 74, 69.1, 252.3, 320.1, 7.1; 530/811, 812, 815, 823; 536/22.1

[56] References Cited

U.S. PATENT DOCUMENTS

| | | | |
|---|---|---|---|
| 4,818,695 | 4/1989 | Elgtved | 435/134 |
| 5,173,417 | 12/1992 | Takeda et al. | 435/198 |
| 5,191,071 | 3/1993 | Kirk et al. | 536/4.1 |
| 5,273,898 | 12/1993 | Ishii | 435/198 |

FOREIGN PATENT DOCUMENTS 9324619 12/1993 WIPO .

OTHER PUBLICATIONS

Fischer and Messner, "Adsorption of lipase on pulp fibers during biological pitch control in paper industry", Enzyme MicrobTechnol (1992) 14:470–473.

Uppenberg et al, The sequence, crystal structure determination and refinement of two crystal forms of lipase B from Candid antarctical Structure (1994) 2:293–308.

*Primary Examiner*—Charles L. Patterson, Jr.
*Assistant Examiner*—Daniel S. Mytelka
*Attorney, Agent, or Firm*—Steve T. Zelson, Esq.; Valeta Gregg, Esq.

[57] ABSTRACT

A new species of the genus Hyphogyma is disclosed, as are new lipases obtainable therefrom, Also disclosed is a process for obtaining the enzymes.

24 Claims, 6 Drawing Sheets

Fig. 5

LF 132 N-terminal

```
  F  T  P  F  P  T  G  A  D  P  A  F  T  Q  S  Q  A  T  L  D  A

  TTCACACCATTCCCAACAGGAGCAGACCCAGCATTCACACAATCACAAGCAACACTAGACGCA
     T  C  C  T  C  C  C  C  T  C  C  T  C  G  C  G  C  C  C  T  C
        G  G     G  G  G  G     G  G     G     G     G  G  G     G
        T  T     T  T  T  T     T  T     T     T     T  T  T     T
                                             AGC         TTA
                                               T           T


CGGAATTCTTCACACCATTCCCAAC                                3831
                    C  C  T  C                           17 mer PCR primer+
                    G  G     G                           handle
                    T  T     T                           deg: 128


3832                                               3' GTCCGATGAGAACTGCGCCTAGGGC
17 mer PCR primer +                                      T  C  C  C
handle                                                      G  G  G
deg:128                                                     T  T  T


Primer 4009          ACGGGCGCAGACCCGGCCTTCACTCAATCTC
31 mer
```

LIPASES FROM HYPHOZYMA

CROSS-REFERENCE TO RELATED APPLICATIONS

This application is a 371 of PCT/DK93/00194 filed Jun. 3, 1993, which is incorporated herein by reference.

TECHNICAL FIELD

The present invention relates to novel microorganisms and to novel enzymes obtainable therefrom. More specifically, the invention relates to a new species of the genus Hyphozyma, and to novel lipases obtainable therefrom, The invention also relates to a process for obtaining the enzymes, immobilized lipase preparations, and industrial applications of these enzymes in the paper pulp industry, for use in ester hydrolysis, ester synthesis or interesteri- fication, and for manufacmre of leather.

BACKGROUND ART

When resinous wood species are used in pulping processes, particularly mechanical pulping processes, pitch problems arise. This widespread phenomenon causes production intermptions and a decreased paper product quality.

Pitch contains considerable amounts of triglycerides, more commonly known as fats, and other esters. Faty acid glyceride hydrolysing enzymes, in the following called lipases, may advantageously be used for efficient hydrolysis of water-insoluble esters, particularly triglycerides.

In order to comply with the prerequisite for paper pulp processing, lipases applied in methods for enzymatic pitch control should be acidophilic and thermophilic.

Enzymes suggested in the prior art for pitch control include lipases derived from strains of Pseudomonas, Humicola, Candida, Chromobacter and Aspergillus.

Some of these lipases are markedly thermophilic, others are markedly acidophilic, but none of these lipases possess both characteristics.

Hyphozyma is a nlew genus of yeast-like Hyphomycetes (vide de Hoog, G. S. & Smith, M.Th.; Antonie van Leeuwenhoek 47 (1981) 339–352), and the following species are reported: *H. vanabilis, M. variabilis* var. odora, *H. sanguinea,* and *H. roseoniger.* However, no lipase production has previously been ascribed to these organsms.

SUMMARY OF THE INVENTION

We have now found that a new species of Hyphooma is able to produce lipase. Moreover, we have found that these novel lipases possess excellent paper pulp processing possibilities due to their markedly thermophilic and acidophilic characteristics. Moreover, we have also found that these novel lipases are well suited for use in ester hydrolysis, ester synthesis or iteresterification, and vafious other industrial applications.

Accordingly, in its first aspect, the present invention provides a biologically pure culture of a species belonging to the genus Hyphozyma, which has the ability to produce lipase. In a more specific embodiment of this aspect, the invention provides a biologically pure culture of a new species represented by the strain Hyphozyma sp. LF132, CBS 648.91.

In its most specific embodiment of this aspect, the invention provides a biologically pure culture of the strain Hyphogyma sp. LP132, CBS 648.91, or mutants or variants thereof.

In its second aspect, the present invention provides a lipolytic enzyme being immunologically reactive with an antibody raised against a purified lipase derived from the strain Hyphozyma sp. LF132, CBS 648.91.

In its third aspect, the present invention provides a lipolytic enzyme comprising one or more of the following partial no acid sequences: Phe TbrPro Phe Pro (SEQ ID NO:4); Thr Gly Ala Asp Pro (SEQ ID NO:5); Ala Phe Thr Gln Ser (SEQ ID NO:6); Gln Ala Thr Leu Asp Ala Gly Leu Thr (SEQ ID NO:7); Gly Ser Gly Ser Lys (SEQ ID NO:8); Val Pro Val Leu Thr Trp Ser (SEQ ID NO:9); Thr Trp Ser Gln Gly Gly Leu Ala Ala GOn (SEQ ID NO:10); Ala Gin Gin Lys Leu Asp Ser Ala Ala Ile Ile Leu (SEQ ID NO:11); Val Ala Gly Lys Asa lie Val Thr Gly Pro Lys Gln (SEQ ID NO: 12); Asn Cys Glu Pro Asp Leu Met Pro Tyr Ala Arg Lys Tyr (SEQ ID NO: 13); and Arg Ile Gly Lys Lys Thr Cys Ser Gly Val Ile Thr Gly (SEQ ID NO:14).

In a more specific embodiment of this aspect, the present invention provides a lipolytic enzyme comprising one or more of the following partial ano acid sequences: Phe Thr Pro Phe Pro Thr Gly Ala Asp Pro (SEQ ID NO:15); Ala Phe Thr Gln Ser Gln Ala Thr Leu Asp Ala Gly Leu Thr (SEQ ID NO: 16); Gly Ser Gly Ser Lys Val Pro Val Leu Thr Trp Ser (SEQ ID NO:17); Thr Trp Ser Gln Gly Gly LeU Ala Ala Gin Trp Ala Leu Thr (SEQ ID NO: 18); Ala Gin Gln Lys Leu Asp Ser Ala Ala Ile Ile Leu Val Ala Gly Lys Asn Ile Val Thr Gly Pro Lys Gln (SEQ ID NO: 19); and Asn Cys Glu Pro Asp Leu Met Pro Tyr Ala Arg Lys Tyr Arg Ile Gly Lys Lys Thr Cys Ser Gly Val Ile Thr Gly (SEQ ID NO:20).

In its fourth aspect, the present invention provides a lipolytic enzyme has the following N-terminal amino acid sequence: Phe Thr Pro Phe Pro Thr Gly Ala Asp Pro Ala Phe Thr Gln Ser Gln Ala Thr Leu Asp Ala Gly Leu Thr (SEQ ID NO:1); or a sequence homologue thereto.

In its fifth aspect, the present invention provides a lipolytic enzyme comprising the following partia amino acid sequence: Gly Ser Gly Xaa Xbb Lys Xaa Xaa Xaa Xaa Xaa Xaa Ser* Gin Gly Gly (SEQ ID NO:21); in which sequence Ser* represents the catalytically active serine, Xaa represents any of the naturally occi amino acids, and Xbb represents a deletion or any of the naturally occurring amino acids except Asn.

In a more specific embodiment of this aspect, the invention provides a lipolytic comprising the following partial amino acid sequence: Gly Ser Gly Xaa Xbb Lys Xaa Pro Xaa Xaa Xaa Xaa Ser* Gin Gly Gly (SEQ ID NO:22), in which sequence Ser* represents the catalytically active serine, Xaa rpresents any of the naturally occurring amno acids, and Xbb represents a deletion or any of the naturally occurring amino acids except Asn.

In a further specific embodiment of this aspect, the invention provides a lipolytic enzyme comprising the following partial amino acid sequence: Gly Ser Gly Xaa Xbb Lys Xaa Pro Xaa Xaa Thr Xaa Ser* Gln Gly Gly (SEQ ID NO:23); in which sequence Ser* represents the catalytically active serine, Xaa represents any of the naturally occuing amino acids, and Xbb represents a deletion or any of the naturally occurring amino acids except Asn.

In a flier specific embodiment of this aspect, the invenuion provides a lipolytic enzyme comprising the following partial amino acid sequence: Gly Ser Gly Xaa Xbb Lys Xaa Pro Xcc Xcc Thr Xaa Ser* Gin Gly Gly (SEQ ID NO:24); in which sequence Ser* represents the catalytically active serrine, Xaa represents any of the natWauy occurring amino acids, Xbb represents a deletion or any of the naturally occurring amino acids except Asn, and Xcc represents a hydrophobic amino acid.

In a further specific embodiment of tis aspect, the invention provides a lipolytic enzyme comprising te following partial amino acid sequence: Gly Ser Gly Xaa Xbb Lys Xaa Pro Val Lcu Thr Xaa Ser* Gln Gly Gly (SEQ ID NO:25); in which sequence Ser* represents the catalytically active serine, Xaa represents any of the naturally occurring a o acids, and Xbb represents a deletion or any of the naturally occurring a acids except Asn.

In a further specific embodiment of this aspect, the invention provides a lipolytic enzyme comprising the following partial amino acid sequence: Gly Ser Gly Ser Xbb Lys Val Pro Val Leu Thr Xaa Ser* Gln Gly Gly (SEQ ID NO:26); in which sequence Ser* represents the catalytically active serine, Xaa represents any of the naturally occurring amino acids, and Xbb represents a deletion or any of the naturally occurring amino acids except Asn.

In a further specific embodiment of this aspect, the invention provides a lipolytic enzyme having the amino acid sequence disclosed as SEQ ID NO 3 of the attached amio acid sequence listing, or a sequence hornologue thereto, In its sixth aspect, the present invention provides a process for obtaiing a lipolytic enzyme of the invention, which process comprises cultivation of a lipase producing strain of the genus yphozyma in a suitable nutrient medium, containing carbon and nitrogen sources and inorganic salts, followed by recovery of the lipolytic enzme.

In its seventh aspect, The present invention provides a process for obtaining a lipolytic enzyme of the invention, the process comprising isolating a DNA fragment encoding the lipolytic enzyme, combining the DNA fragment with appropriate expression signal(s) in an appropriate vector, introducing the vector or parts thereof into an appropriate host either as an autonomously replicating plasmid or integrated into the chromosome, cultivating the host organism under conditions leading to expression of the lipolytic enzyme, and recovering the lipolytic enzyme from the culture medium.

In its eighth aspect, the present invention relates to the use of a lipolytic enzyme of the invention in the paper pulp industry for enzymatic pitch control.

In its ninth aspect, the present invention provides an immobiized lipase preparation obtained by imobilization of the lipolytic enzyme of the invention.

In its tenth aspect, the present invention relates to the use of a lipolytic enzyme of the invention, and/or an imnmobilized lipase preparation of the invention, for ester hydrolysis, ester synthesis or interesterification.

In its eleventh aspect, the present invention provides a process for preparation of monoesters of glycosides in the presence of a lipolytic enzyme of the invention, and/or an immobilied lipase preparation of the invention.

BRIEF DESCRIPTION OF DRAWINGS

The present invention is further illustrated by reference to the accompanying drawings, in which.

FIG. 5 shows three primers (#3831, 17 mer PCR primary+handle, deg. 128; #3832, 17 mer PCR primer+handle, deg. 128; and #4009, 31 mer), designed on basis of the N-terminal amino acid sequence of a lipolytic enzyme of the invention.

DETAILED DISCLOSURE OF THE INVENTION

The Microorganisms

Figure 1:
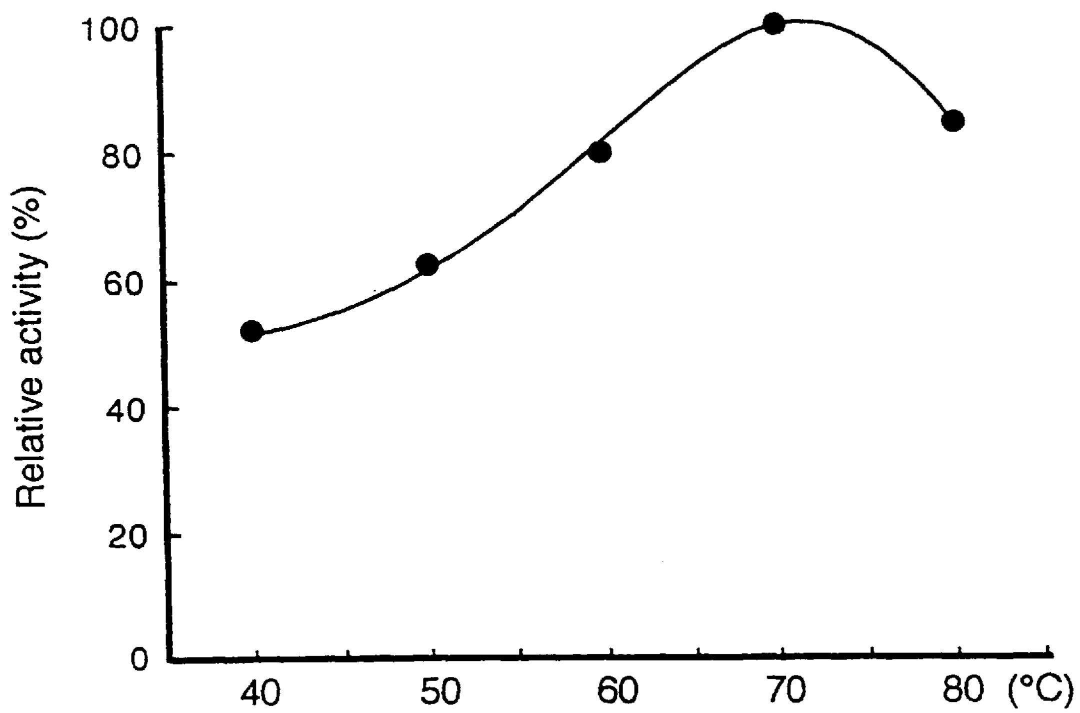
FIG. 1 shows the temperature, activity (% relative) at pH 6.0 of a lipolyuic enzyme of the invention.

The present invention provides a biologicall y pure culture of a strain of Hyphozyma, which has the ability to produce lipase.

In a more specific aspect, the invention provides a biologically pure culture of a new species represented by the strain Hyphozyma sp. LF132, CBS 648.91. The representative isolate of these novel microorganisms of the invention, designated Hyphozyma sp. LF132, has been deposited on Nov. 12, 1991, for the purpose of patent procedures according to the Budape st Treaty on the rtelational Recognition of te Deposits of Microorglsms, at Centraal Bureau voor Schienzymelculotres (CBS), Oosterstraat 1, 3740 AG Baarn, Netherlands, and is given the accession number CBS 648.91.

In a further specific aspect, the invention provides a biologically pure culture of a strain of microorganisms being essentially identical with the native Hyphozyma sp. LF132, CBS 648.91, or mutants or variants thereof.

The microorganism of the invention can be cultivated under aerobic conditions in a nutrient medium containing assimilable carbon and nitrogen together with other essential nutrients, the medium being composed in accordance with the principles of the known art.

Suitable carbon sources are carbohydrates such as sucrose, glucose and starch, or carbohydrate containing materials such as cereal grain, malt, rice and sorghum. The carbohydrate concentration incorporated in the medium may vary widely, e.g. up to 25% and down to 1–5%, but usually 8–10% will be suitable, the percentages being calculated as equivalents of glucose.

The nitrogen source in the nutrient medium may be of inorganic and/or organic nature. Suitable inorganic nitrogen sources are nitrates and ammonium salts. Among the organic nitrogen sources quite a number are used regularly in fementation processes involving the cultivation of microorganisms. Mustrative examples are soybean meal, cotton seed meal, peanut meal, casein, corn, corn steep liquor, yeast extract, urea and albumin. In addition, the nutrient medium should also contain usual trace substances.

The cultivation is preferably conducted at pH 4–9, which can be obtained by addition of suitable buffers after sterilization of the growth medium. For cultivation in tank fermentors it is necessary to use arifcial aeration. The rate of aeration is similar to that used in conventional tank fermentation.

After fermentation, liquid enzyme concentrates may be produced by removal of coarse material from the broth or, if desired, concentration of the broth by evaporation at low temperature, or by ultrafiltration or reverse osmosis, Finally, preservatives may be added to the concentrate, Solid enzyme preparations may be prepared from the purfied and/or concentrated broth by precipitation with salts, such as $Na_2SO_4$, or water-miscible solvents, such as ethanol or acetone. Removal of the water in the broth by suitable drying methods, such as spray-drying, may also be employed.

The Enzymes

The novel lipolytic enzymes of the invention can be described by any of the following characteristics.

Structural Progerties

A lipolytic enzyme of ft invention comprises one or more of the following partial amino acid sequences: (&) Phe Thr Pro Phe Pro (SEQ ID NO:4); (b) Thr Gly Ala Asp Pro (SEQ ID NO:5); (c) Ala Phe Thr Gln Ser (SEQ ID NO.6); (d) Gln Ala Thr Leu Asp Ala Gly Leu Thr (SEQ ID NO:7); (e) Gly Ser Gly Ser Lys (SEQ ID NO:8); (f) Val Pro Val Leu Thr Trp Ser (SEQ ID NO:9); (g) Thr Trp Ser Gln Gly Gly Leu Ala Ala Gln (SEQ ID NO:10); (h) Ala Gln Gln Lys Leu Asp Ser Ala Ala Ile Ile ILeu (SEQ ID NO:11); (i) Val Ala Gly Lys Asn Ile Val Thr Gly Pro Lys Gln (SEQ ID NO: 12); (j) Asn Cys Glu Pro Asp Leu Met Pro Tyr Ala Arg Lys Tyr (SEQ ID NO:13); and (k) Arg Ile Gly Lys Lys Thr Cys Set Gly Val Ile Thr Gly (SEQ ID NO:14).

In a more specific aspect, a lipolytic enzyme of the invention comprises one or more of the following partial amino acid sequenres.- (a) Phe Thr Pro Phe Pro Thsr Gly Ala Asp Pro (SEQ ID NO:15); (b) Ala Phe Thr Gln Ser Gln Ala Thr Leu Asp Ala Gly Leu Thr (SEQ ID NO:16); (c) Gly Ser Gly Ser Lys Val Pro Val Izu Thr Trp Ser (SEQ ID NO; 17); (d) Thr Trp Ser Gin Gly Gly Leu Ala Ala Gln Trp Ala Leu Thr (SEQ ID NO:18); (e) Ala Gln Gln Lys Leu Asp Ser Ala Ala Ile Ile Leu Val Ala Gly Lys Asn Ile Val Thr Gly Pro Lys Gln (SEQ ID NO: 19); and (f) Asa Cys Glu Pro Asp I=u Met Pro Tyr Ala Arg Lys Tyr Arg Ile Gly Lys Lys Thr Cys Ser Gly Val lie Thr Gly (SEQ ID NO:20).

In a further specific aspect, a lipolytic enzyme of the invention bas fte following N-terminal amino acid sequence: Phe Thr Pro Phe Pro Thr Gly Ala Asp Pro Ala Phe Thr Gin Ser Gln Ala Thr Leu Asp Ala Gly Leu Thr; or a sequence homologue thereto.

In a further specific aspect, a lipolytic enzyme of the invention comprises following paxtial amino acid sequence: Gly Ser Gly Xaa Xbb Lys Xaa Xaa Xaa Xaa Xaa Xaa Ser* Gln Gly Gly (SEQ ID NO:21).

In a further specific aspect, a lipolytic enzyme of the invention comprises the following partial amino acid sequence: Gly Ser Gly Xaa Xbb Lys Xaa Pro Xaa Xaa Xaa Xaa Ser* Gln Gly Gly (SEQ ID NO:22).

In a further specific aspect, a lipolytic enzyme of the invention comprises the following partial amino acid sequence: Gly Ser Gly Xaa Xbb Lys Xaa Pro Xaa Xaa Thr Xaa Ser* Gln Gly Gly (SEQ ID NO:23).

In a further specific aspect, a lipolytic enzyme of the invention comprises the following partial amino acid sequence: Gly Ser Gly Xaa Xbb Lys Xaa Pro Xcc Xcc Thr Xaa Ser* Gln Gly Gly (SEQ ID NO:24).

In a further specific aspect, a lipolytic enzyme of the invention comprises the following partial a o acid sequence: Gly Ser Gly Xaa Xbb Lys Xaa Pro Val Leu Thr Xaa Ser* Gln Gly Gly (SEQ ID NO:25).

In a further specific aspect, a lipolytic enzyme of the invention comprises the following partial amino acid sequence: Gly Ser Gly Ser Xbb Lys Val Pro Val Leu Thr Xaa Ser* Gln Gly Gly (SEQ ID NO:26).

In the above paal amino acid sequences Ser* represents the catalytically active serine, Xaa represents any of the naturally occurrig amino acids, Xbb represents a deletion or any of the naturally occing amino acids except Asn, and Xcc represents a hydrophobic amino acid.

In a further specific aspect, a lipolytic enzyme of the invention has the amino acid sequence disclosed as SEQ ID NO 3 of the attached amino acid sequence listng, or a sequence homologue thereto, Table of Amino Acids

| One-letter symbol | | Trivial name Symbol | | |
|---|---|---|---|---|
| A | = | Ala | = | Alanine |
| C | = | Cys | = | Cysteine |
| D | = | Asp | = | Aspartic acid |
| E | = | Glu | = | Glutamic acid |
| F | = | Phe | = | Phenylalanine |
| G | = | Gly | = | Glycine |
| H | = | His | = | Histidine |
| I | = | Ile | = | Isoleucine |
| K | = | Lys | = | Lysine |
| L | = | Leu | = | Leucine |
| M | = | Met | = | Methionine |
| N | = | Asn | = | Asparagine |
| P | = | Pro | = | Proline |
| Q | = | Gln | = | Glutamine |
| R | = | Arg | = | Arginine |
| S | = | Ser | = | Serine |
| T | = | Thr | = | Threonine |
| V | = | Val | = | Valine |
| W | = | Trp | = | Tryptophan |
| Y | = | Tyr | = | Tyrosine |
| B | = | Asx | = | Asp or Asn |
| Z | = | Glx | = | Glu or Gln |
| X | = | Xaa | = | Unknown or "other" amino acid |

* = deletion or absent amino acid

In the present context, tle term "hydrophobic amino acid" encompasses a naturly occurring amino acid having nonpolar or hydrophobic side groups, and includes the following seven amino acids: Ala, Val Leu, Ile, Met, Phe, and Trp.

Homology

In the present context, the term "homologue" is intended to encompass an amino acid sequence which is at least 75%, preferably at least 85%, most preferred at least 90%, homologous to the sequence referred to. The term is intended to include modifications of the amino acid sequence, which may result in a different protein structure and a lipase mutant with different properties than the native enzyme.

Origin

In a preferred embodiment, the lipolytic enzyme of the invention is derivable from a strain belonging to the genus Hyphozyma.

In a more preferred embodiment, the lipolytic enzyme of the invention is derivable from a strain belonging to the species represented by the strain Hyphozyma sp. LP132, CBS 648.91.

In a yet more preferred embodiment, the lipolytic enzyme of the invention is derivable from the strain Hyphozyma sp. LP132, CBS 648.91, or a mutant or a variant thereof.

Physico-Chemical Properties

In another preferred embodiment, the lipolytic enzyme of the invention has more than 80% relative activity in the pH range of from 4.0 to 6.0 (when deternmied at 70° C.).

In yet another preferred embodiment, the lipolytic enzyme of the invention has a molecular weight of approximately 38–40 kD as detenmned by SDS-PAGE.

In a further preferred embodiment, the lipolytic enzyme of the invention has an apparent pI of approximately 6.3, determined by isoelectric focusing on LKB Ampholine® PAG plates.

In a further preferred embodiment, the lipolytic enzyme of the invention is positionally non-specific.

Immunochemical Properties

The lipolytic enzyme of the invention is immunologically reactive with an antibody raised against a purified lipase derived from the strain Hphoyrma sp. LF132, CBS 648.91, i.e. has irmmunochemical properties identical or partially identical (i.e. at least partally identical) to those of a lipase derived from the strain Hyphozyma sp. LF132, CBS 648.91.

The immunomechanical properties can be determined immunologically by cross-reaction identity tests. The identity tests can be performed by the Well-known Ouchterlony double immunodiffusion procedure or by tandem crossed inmunoelectrophoresis according to Axelsen N. H.; Handbook of Immunoprecipitation-in-Gel Techniques; Blackwell Scientific Publications (1985), chapters 5 and 14. The terms "antigenic identity" and "partial antigenic identity" are described in the same book, Chapters 5, 19 and 20.

Processes for Obtaining the Lipase

The lipolytic enzyme of tlhe invention is obtainable by cultivation of a microorganism of the invention, preferably the strain Hyphozyma sap LP132, CBS 648.91, or a mutant or a variant thereof, in a suitable nutrient medium, containing carbon and nitrogen sources and inorganic salts, followed by recovery of the enzyme by methods known per se.

The lipolytic enzyme may also be obtained by recombinant DNA-technology by methods known in the art per se, e.g. isolating a DNA fragment encoding the lipolytic enzyme, combining the DNA fragment with appropriate expression signal(s) in an appropriate vector, introducing the vector or parts thereof into an appropriate host either as an autonomously replicating plasmid or integrated into the chromosome, cultivating the host organism under conditions leading to expression of the lipolytic enzyme, and recovering the lipolytic enzyme from the cult=re medium.

In a preferred embodiment, the process comprises cultivating a host organism being, an *Escherichia coli,* a member of the genus Bacillus, Streptonyces or Saccharomyces.

In a more specific embodiment, the process comprises cultivating a host organism being a filentous fungus, preferably a member of the genus Aspergillus.

In a yet more specific embodiment, the process comprises cultivating a host organism being *A. oryzae* or *A. niger.*

In another embodiment, the process comprises isolating a DNA fragment having the nucleotide sequence disclosed as SEQ ID NO 2 of the attached sequence listing, or a sequence homologue thereto.

Immunobilization of the Lipase

Imobilized lipase denotes lipase in the form of immobilized enzyme or immobilized cells, as defined in "Guidelines for the characterization of immobilized biocatalysts" (1983), Enzyme Microb. Technol., 5 304–397.

For the practice of this invention, the lipolytic enzyme may be irmnobilized by any method known in the art, e.g- as described in Mosbach K (ed.): Methods in Enzymology, 44, "immobilized Enzymes" (Academic Press, 1976). AvailabIe methods for enzyme immobilization include cross4ining of cell homogenates, covalent coupling to insoluble inorganic or organic carriers, entrapment in gels, and adsorption on ion-exchange resins or other adsorbent materials. Also, coating on a particulate support may be used, as described in *Macrae A. R. and Hammond R C (*1985), Biotechnology and Genetic Engieering Reviews, 3 193

A preferred immobilization method uses a particulate, macroporous resin. The lipolytic enzyme may be simply adsorbed on the resin, or it may be attached to the resin by cross-linking with glutaraldehyde or other cross-likig agents known in the art.

A preferred resin type is weakly basic anion exchange resin, e.g. acrylic, polystyrene or phenolformaldehyde. Another preferred resin type is an adsorbent resin of the phenol-formaldehyde type. Yet another preferred resin type is adsorbent resin, e.g. a porous aliphatic olefmic polymer, or of an acrylic type.

Another preferred immobilization method uses an inorganic support material, and the lipolytic enzyme is preferably attached to te support by adsorption or covalent coupling. Such support materials and immobilization techniques are described in Mosbach K, op. cit.

In yet another preferred immobilization method, the lipolytic enzyme is immobilized on inorganic materials by adsorption, covalent coupling or precipitation, preferably on zeolites, celites, porous glass beads, glass wool, aluminium oxides, kieselguhr, selicagel, or clay.

In a fulrther preferred immobilization method, the lipolytic eriyme is immobilized on particles of naturally occurring organic materials, preferably bone particles, chitin, chitosa, or agar.

Enzymatic Pitch Control

The invention also relates to the use of a lipolytic enzyme of the invention in a method for enzymatic pitch control.

In the context of this invention, a method for enzymatic pitch control is meant to indicate a method for avoiding pitch troubles that arise in production processes for mechanical pulp or paper-making processes using mechanical pulp. Methods for enzymatic pitch control involve hydrolysis of water-insoluble esters or resins present in the paper pulp.

A method for enzymatic pitch control may be conducted essentially as described in e,g. Intmational Patent Publications WO 92/07138, WO 92/13130, WO 92/18638, and WO 92/19808.

In a more specific embodiment, a lipase dosage of 0.5–150 KLU/kg pulp, preferably 20–75 KLU/kg pulp, most preferred 5–20 KLU/kg pulp (dry substance) is used.

In another specific embodiment, the method is conducted at ph 3–7, preferably 4–7, at a temperature of 40°–90° C., preferably 50°–70° C. at a reaction time of 0.5–5.0 preferably 2.5–4 hours, and a pulp consistency of 2–30 %, preferably 3–8% (w/w).

Lipase-catalyzed Processes

Due to its excellent thermal stability, the lipolytic enzyme of the invention is advantageously employed in processes performed at elevated temperatures, e.g. synthesis/hydrolysis reactions involving lipids. Moreover, Fe lipolytic enzyme of the invention is a highly efficient catalyst due to high conversion and low by-product formation.

The lipolytic enzyme of the invention may be used in any of the following lipase-catalysed processes (reactants indicated in parenthesis):

A) Ester hydrolysis (ester+water)

B) Ester synthesis (acid+alcohol)

C) Interesterification, including:

i) Acidolysis (ester+acid)

ii) Alcoholysis (ester+alcohol)

iii) Ester interchange or transesterification (ester+ester)

The alcohol may be mono- or polyvalent primary and/or secondary alcohol or a mixture of these. The acid may be any carbox:ylic acid or a mixtue of these. The ester may be any ester derived from the mentioned alcohols and acids, or a mixtlre of these.

Some advantageous process embodiments are described in e.g. International Patent Publication WO 88/02775, which publication is hereby incorporated by reference.

In another preferred embodiment, the lipolytic enzyme of the invention may be used for enzymatic preparation of monoesters of glycosides as described in e.g. U.S. Pat. Nos. 5,191,071 and 5,200,328, which publications are hereby incorporated by reference.

Other Industrial Aplications

Among other industrial applications the lipolytic enzyme of the invention may be used for enzymatic manufacture of leather by method known in the an, in order to improve the degreasing of hides and sins, to reduce the use of emulsifiers, and as a substitute for solvents.

The lipolytic enzyme of the invention can be added either in the soaking, liming or bating, preferably as early in the beamiouse processes as possible. This allows the enzyme sufficient time to operate.

The following examples frer illustrate the present invention, and they are not intended to be in any way limiting to the scope of the invention as claimed.

EXAMPLE 1

Cultivation Example

The strain Hyphozyma sp. LF132, CBS 648.91, was cultivated in a nutrient medium containing the following components (per litre):

| | |
|---|---|
| Glucose | 20 g |
| Peptone | 10 g |
| $MgSO_4$, $7H_2O$ | 1 g |
| Yeast Extract | 10 g |
| $K_2HPO_4$ | 5 g |
| pH adjusted to 6.5 with NaOH | |

The strain was cultivated at 30° C. for 3 days. The culture broth was subjected to liquid/solid separation by centriftgation, and the supernatant was freeze-dried resulting in a crude powder preparation.

Lipase Activity

After centrifugation, a lipase activity of 2 units/g culture broth was obtained, 1 unit being equivalent to the amount of lipase that releases one limol of fatty acid per minute from emulsified olive oil at 40° C. and pH 4.5. The amount of released fatly acid is determined by TLC-FID analysis (Iatroscan™).

Characterization

The crude powder preparation was characterized by its pH and temperature profile.

The temperamre profile was determined at pH 6.0 in a range of from 40° C. to 80° C. The lipase was incubated for 10 minutes, and the activity was determined by the method described above.

The temperature profile is presented in FIG. 1 as relative activity (setting the activity at 70° C. equal to 100%). From the figure it appears that Htle lipase is active at temperatures of from below 40° C. to above 80° C. The temperature optimum of this crude lipase preparation lies in the range of from 60° C. to 80° C., more specifically around 70° C.

The pH profile was determined at 70° C. The lipase was incubated for 10 minutes, and the activity was determined by the method described above.

Figure 2:
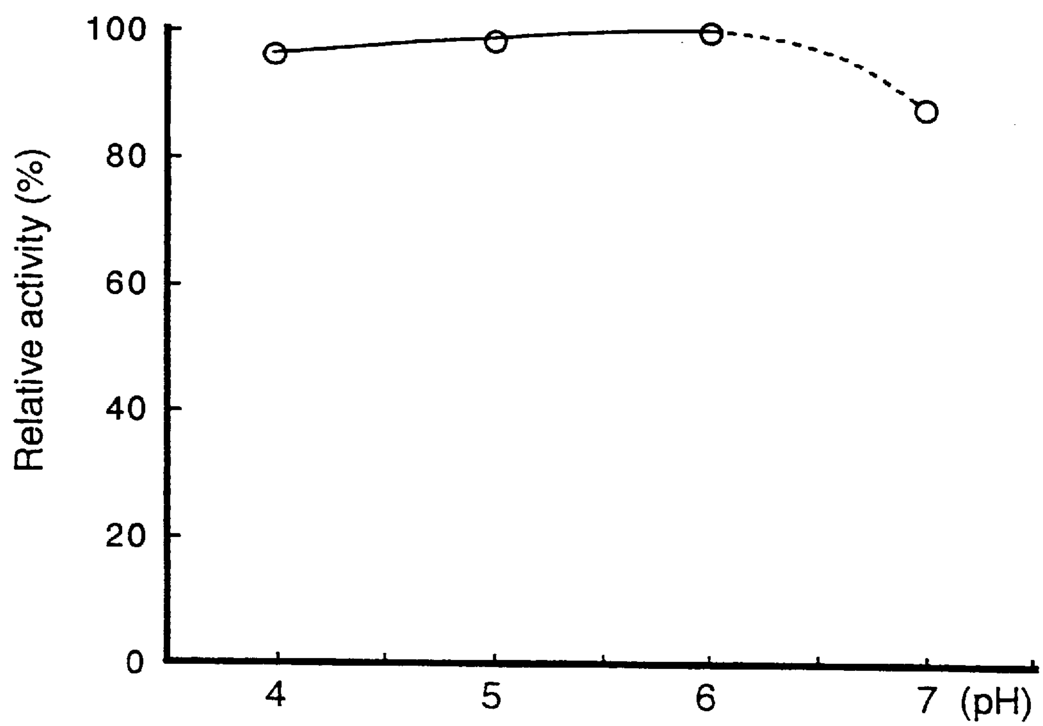
FIG. 2 showsetine pH activity (% relative) at 70° C. of a lipolytic enzymae of the invention

The pH profile is presented in FIG. 2 as relative activity (setting the activity at pH 6.0 equal to 100%). Due to a change of buffer system (citrate, phosphate buffer), the figure is made up of two curves, one representing the interval of from pH 4.0 to 6.0, inclusive, the other representing the inxerval of from pH 6.0 to 7.0, inclusive. From (be figure it appears that the lipase is active at pH values of from below 4,0 to above 7.0. No significant pH optimum has been determired, although it appears to be around pH 6.0. However, it also appears that the lipase has more tan 80% relative activity widtin the interval pH 4.0–6.0, preferably more than 90% relative activity in the interval pH 4.0–6.0, when determined at 70° C.

The lipase was found to act positionally non-specific.

Partial Purification 4.0 g of the above crude powder preparation were dissolved in 50 ml 20 mM phosphate buffer, pH 7.2, containing 0.2 M sodium sulfate. The solution was applied on a phenyl sepharose FF column (Pharmacia® LKB Biotechnology AB).

Lipase was eluted with 0.25 mM phosphate buffer, desalted by ultrafiltration, and freeze dried.

300 mg of purified lipase of 15,000 lipase units/g, as described above, were obtained.

EXAMPLE 2

Pulp Treatment

In this example, the use of a lipase of the invention for triglyceride hydrolysis in paper pulp is demonstrated in laboratory-scale.

In a first experiment, 500 g of 4% pulp slurry pH were adjusted with $H_2SO_4$ to 6.5 and 4.5, respectively. 1.5 ml solution containing 100 units of the patially purified lipase obtained according to Example 1 were added. The pulp shory was incubated for 2 hours at 40, 60, 70, and 80° C., respectively, with sting (300 rpm.).

In a second experiment, 500 g of 4% pulp slurry pH were adjusted with $H_2SO_4$ to 4.0, 4.5, 5.0, 6.0, and 7.0, respectively. 1.5 ml solution containing 100 units of the partially purified lipase obtained according to Example 1 were added. The pulp slurry was incubated for 2 hours at 40° C. with stirring (300 rpm.).

Fatty material was extracted from the lipase treated slurry, and from an untreated slurry (reference slurry), respectively. To 150 g of pulp slurry 150 g of water, 200 ml of hexane and 2 ml of internal standard (1% acetyl cholesterol in hexane) were added. The mixture was shaken for 5 minutes in a separatory finnel, and the pulp filtered off. In the separatory funnel famty material was collected in the hexane layer, and obtained by evaporation and redissolution.

Extract was applied on Chromatorod S-III (Iatron aboratories Inc.), and developed with hexane:ether:$NH_4OH$ (60:8:0.2) mixture. The components were detected by FID analysis (latroscant™. The degree of hydrolysis of triglycerides was determined by the calculation:

$$\text{Degree of Hydrolysis} = \frac{TG_0 - TG_R}{T_0}$$

$TG_O$: Amount of triglyceride in reference slurry.
$TG_R$: Amount of triglyceride in lipase-treated slurry.

Figure 3:
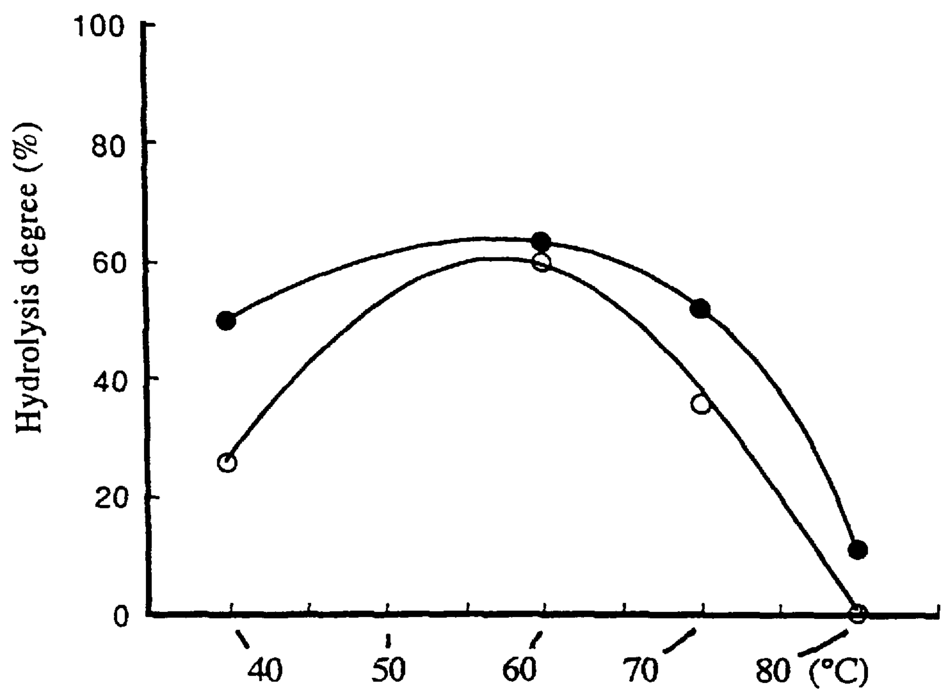
FIG. 3 shows the relation between temperature and the degree of hydrolysis when employing the lipolytic enzyme of the invention to paper pulp (○ determined at pH 6.5;●determined at pH 4.5)
Figure 4:
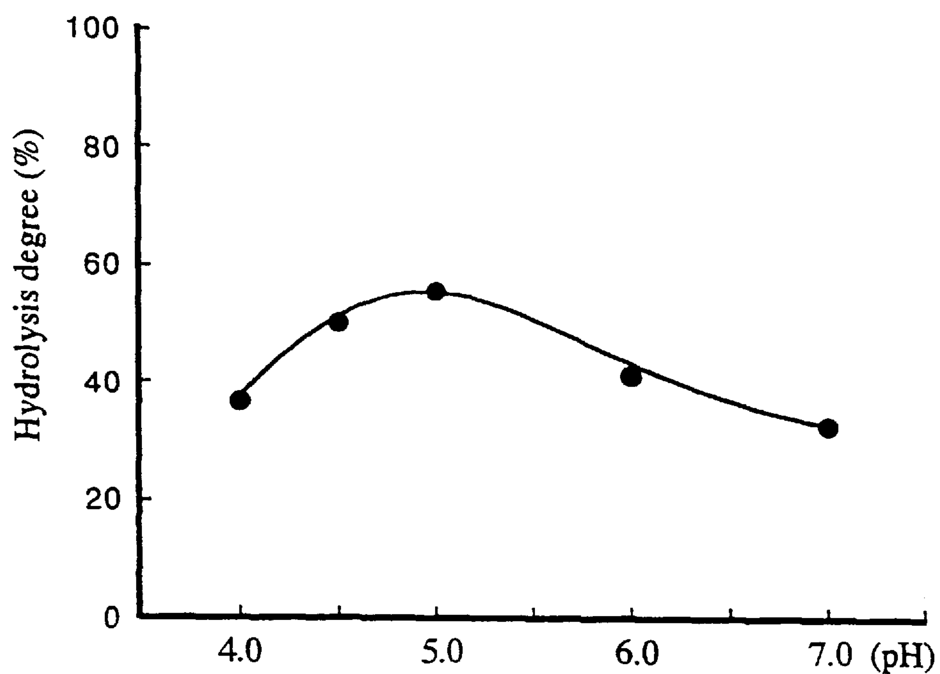
FIG. 4 shows the relation between pH and e degree of hydrolysis when employing the lipolytic enzyme of the invention to paper pulp (determined at 40° C.)

The results of these experiments are presented in FIGS. 3–4. It appears from the figures that the lipase of the invention possesses excellent tdiglyceride hydrolysis in paper pulp in a broad pH range of from pH below 4,0 to pH above 7.0, and in a temperature range of from below 50° to above 70° C.

EXAMPLE 3

Purification Example

In this example, the lipase activity is described by terms of Lipase Units (LU). One LU is the amount of enzyme which, under standard conditions (i.e. at 30.0° C.; pH 7.0; and tributyrine as substrate) liberates 1 $\mu$mol of titratable butyric acid per minute. A folder AF 95/5 describing this analytical method is available upon request to Novo Nordisk A/S, Denmark, which folder is hereby included by reference.

Partially purified, freeze dried lipase powder obtained according to Example 1 (140 to 160 LU/g) was applied on a Butyl-Toyopearl column after adjusting the salt concentration to 0.8M with ammonium acetate. Bound lipase activity was eluted with water.

Fractions contamiflg lipase activity were pooled, concentrated and dialysed against 25 mM Tris acetate buffer, pH 7. The concentrated preparation was passed through a DEAE-sepharose columnn. Effluent containi lipase activity was adjusted to pH 6 and passed through a CM-sepharose column. In both steps, negative adsorption was used to split off impurities.

Finally, pH of the effluent from the CM-sepharose column was adjusted to 9 and ionic strength to 2 mS/cm and applied on 1 ml of Mono-Q column. The bound lipase activity was eluted with a linear salt gradient. The lipase activity was eluted at or around a salt concentration of 0.15M.

Electrophoresis on SDS-PAGE revealed a major band at 38–40 kD) (Pharmacia™Phast method).

EXAMPLE 4

Amino Acid Determination

The LF132 lipase obtained according to Example 3 was concentrated using a Millipore Ultrafree-MC filter unit. Concomitanty the buffer was changed to 50 mM $NH_4HCO_3$.

Folowing concentration, the sample was subjected to N-teournal amino acid sequence determination in an Applied Biosystems 473A sequencer.

This determination resulted in the =bno acid sequence identified by the sequence jsting attached to this specification (SEQ ID NO 1).

EXAMPLE 5

Immobilization Example 100 mg of (dxy substance) Accurel™ EP100 (which is a particulate polypropylene resin as described in AKZO, Fibres and Polymers Division, Accurel Systems Data Sheet, obtainable from ENKA AG, Postfach D-8753 Obernburg, Germany, were slurried in 96% ethanol. The excess of ethanol was sucked away.

Immediately 2 ml of an enzyme solution containig the purified lipase obtained according to Example 3 dissolved in phosphate buffer, 50 mM, 11 pH 6.5, in an amount of 600 LU/ml, were added. The suspension was stirred for 2 hours at room temperature.

Subsequently, the product was filtered and rinsed wit deionized water (10 ml), and dried in a hood.

EXAMPLE 6

Esterification Example

General Methods

HPLC-analysis was performed using a Shimadzu Lt-4 liquid chromatograph equipped with a RID-2A refractive index detector. A $SiO_2$–$NH_2$ Hibar LiChrosorb column (Merck) was used, with 96% ethanol as eluent (Merck, HPLC-grade). TLC-analysis was performed using $SiO_2$-coated alumium sheets (Merck) and toluene/ethylacetate/medanol; methanol; 8:6:3 (vol/vol/vol) as mhobile phase followed by developing by spraying with 2% sulfuric acid and heating to 100° C. As reference was used ethyl 6-O-dodecanoyl D-glucopyranoside prepared according to *Björkling F., Godtfredsen S. E., and Kirk O.* (1989); J. Chem. Soc., Chem. Comm. 14 934–935. $^1$-NMR spectra were obtained on a Bruker acp 300 NMR spectrometer using $CDCl_3$ as solvent (using TMS as reference).

Preparation of Ethyl D-glucopyranoside

D-(+)-Glucose (500 g, 2.8 mol) were suspended in absolute etbanol (1.5L, 25.7 mol). Amberlyst 15 (strongly acidic ion exchange resin, 20 g) were added and the reaction mixture was refluxed under efficient mechanical string. After 16 h HPLC-analysis indicated complete conversion of glucose. The slightly yellow reaction mixture was cooled to room temperature and the ion exchange resin removed by filtration. The crude product was decolorized using activated carbon (5 g), and excess ethanol w%as distilled off under reduced pressure yielding the crude ethyl D-glucopyranoside as a viscous syrup ($^1$H-NMR indicating a 1:1 mixture of the α- and the β-anomer).

Esterification of Decanol with Dodecanoic Acid 150 mg of dodecanoic acid (0.75 mmol) were added to 150 $\mu$l of decanol (0.82 mmol), and the mixture was melted at 60° C. under magnetic stirring. Then, 10 mg of immobilized lipase (prepared as described in Example 5) were added and stirring was continued at 60° C. After 24 hours the ester formation was monitored by analyzing a sample using $^1$H NMR This indicated a conversion of 75 % (monitored by comparing the integral of the signals corresponding to the O-$CH_2$-R group of the ester at 4.05 ppm and the HO-$CH_2$-R group of the unconverted alcohol at 3.63 ppm).

Eserification of Ethyl D-glucopyranoside with Dodecanoic Acid 4 g of ethyl D-glucopyranoside (20 mmol) were mixed with dodecanoic acid (4 g, 40 mmol) at 70° C. using mechanical stirring (125 rpm), Then, 400 mg immobilized lipase (prepared as described in Example 5) were added and stirring was continued at 70° C. at 0.01 bar. The progress of the reaction was followed by HPLC as described above, After 24 hours a con-version of 88% was reached with a byproduct formation (ethyl 2,6-O-dodecanoyl dodecanoyl D-glucopyraoside) of 6%. After 48 hours a conversion of 97% was reached with a by-product formation of 9%.

This example demonstrates the lipase to be a highly efficient catalyst (high conversion, low by-product formation) in the synthesis of 6-O-monoesters of ethyl D-glucopyranoside, a property which is, certainly, not general for lipases as illustrated in several publications (vide e.g. Björkling F, Godtfedsen S. E., and Kirk O. J. Chem. Soc, Chem. Commnun. 1989 14 934; and Adelhorst K, Bj örkling F. Godrfredsen S. E.,and Kirk O, Synthesis, 1990 (2) 111).

EXAMPLE 7

Recombinantly Produced Lipase

Based on the N-terminal amino acid sequence disclosed in Example 4 two PRC primers (#3831 and #3832, cf, FIG. 5) were designed.

Using standard techniques (as described in e.g. *Sambrook, Fritsch and Maniatis* (Eds.), Molecular Cloning, 2. Ed., Cold Spring Harbor Press, 1989), DNA isolated fromn the strain Hyphozyma sp. LF132, CBS 648.91 was used as template in PCR reactions for amplification of a sequence consistent with the N-tenninal sequence. This sequence was cloned as a BamH1-Eco-R1 fragment into pUC19 (Yanish-Perron, er al., Gene 1985 33 103–109). Sequencing this insert in individual *E. coli* transformants as expected showed a degenerate sequence in the areas corresponding to the above primers, while the sequence in between was invariant. A primer (#4009, cf. FIG. 5) corresponding to the invariant sequence was synthesized.

Figure 6:
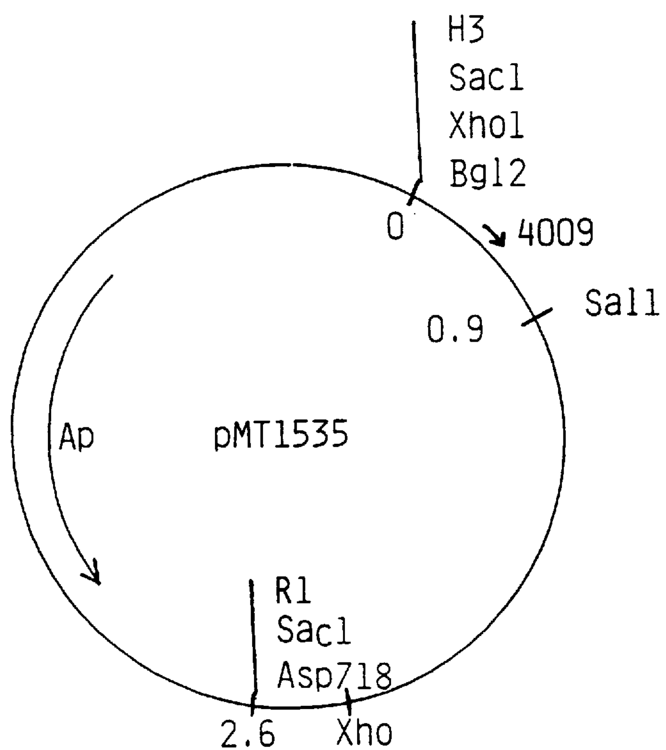
FIG. 6 shows the diagram of plasmid pMT1535.

A Sau3A DNA library of the LF132 lipase (4–10 kb) in BamH1–Bg12 digested pIC19H (Marsh, et al, Gene, 1984 32 481–485) was made. The library was probed with primer #4009, and 5 colonies were characterized and shown by restriction mapping to be overlapping clones. The orientation of the clone was determined by running PCR reactions on the clones with primer #4009 and either of the pUC uni or reverse primers (from New England Biolabs, catalogue Nos. 1212 and 1201, respectively). In summary, the entire gene has been localized and subcloned on an approximately 2.6 kb fragment in which the position of the 4009 primer is at approximately 0.5 kb (pMT1535, cf. FIG. 6).

The part of the pMT1535 insert containing the lipase encoding sequences was subjected to dideoxy sequencing of both strands (cf. SEQ ID NO 2). The N-terminal to acid sequence of tihe mature lipase determined in Example 4 was found to be fully in accordance with the sequence withl phenylalanine in position 23 of the deduced prmary translation product.

The deduced mature protein consists of 319 amino acids with a calculated molecular weight of 33451 D (cf. SEQ ID NO 3).

Primers #4328 (CGGGATCCTGCAACATGAAGCICTCG) (SEQ ID NO:27) and #4329 (CGGGATCCTCATCCAGTGATGACGC) (SEQ ID NO:28) were used to introduce BamH1 sites 5' and 3' to the lipase encoding sequence in a PCR product from the above pMT1535. The lipase sequence was confirmed in the pUC19 cloned PCR product. The BamH1-BamH1 fragment was cloned into the vector part of a pMKan37 plasmid, obtained as follows.

The p960 plasmid, described in EP Patent Application 305,216 and used for expression of *Humicola lanuginosa* lipase, was modified by replacing 60 basepairs of the 5'untranslated region of the *Aspergillus oryzae* TAKA promotor just upstream to the *Humicola lanuginosa* lipase encoding gene with the corresponding 5' untranslated region from the *Aspergillus nidulans* TPI (triosephosphate isomerase) gene. A synthetic oligonucleotide containing the 5' untranslated region from *A. nidulans* TPI (triosephosphate isomerase) gene, and flanked at each end by 20 bases homologous to p960 sequences just outside the untranslated region, was used in a PCR reaction together with another primer covering the BssHII site in the TAKA promotor region. As the mutagenization primer covers the BAMHII site close to the ATG start codon, the PCR fragment was digested with Bam11 and BssHII, and recloned into p960 digested with BssHII and partially with BamH1, to give the above pMWan37 plasmid.

The BamH1–BamH1 fragment derived from pMT1535 as described above was cloned into the BamH1 cut and dephosphorylated vector pMHan37. The orientation of the insert was checked by restriction mapping, and one plasmid, pMT1562, in which the LF132 lipase sequence was oriented so as to be under the control of the fingamyl promoter in the expression cassette [Fungamyl promotor—TPI 5' untranslated—preproLF132Hipase—AMG terminator] was obtained.

pMT1562 was cotransformed into *A. oryzoe* NIBHT 4177 with the selective plasmid pToC90 (obtained according to International Patent Application WO 91/17243). Fifteen transfomants were grown in tubes on YP+2% maltose for four days at 30° C., and the supernatants analyzed by SDS gels and coomassie brilliant blue staining. A standard of LF132 lipase, obtand according to Example 3, was run on the same gel.

Eleven of the transformants appeared to be cotransformants, and from comparison to the standard the best transfonmants were estimated to make approximately 380 mg/litre when cultivated in shake tubes.

EXAMPLE 8

Thermal Stability

A lipase preparation obtaed according to Example 7 was subjected to analysis for thermal stability by Differenti Scanning Calorimetry (DSC). Using this technique, the thermal denaturation temperature, $T_d$, is determined by hearing the enzyme solution at a constant rate and measuring the change in heat capacity during the denaturation process.

The equipment used was a MC2D from MicroCal Inc. connected to a PC. Enzyme solutions were prepared in 50 mM degassed buffer (acetate pH 5; TRIS pH 7–9; and glycine pH 10). Enzyme concentration was approx. 0.8 mg/ml as determined by absorbance at 280 nrm, and a total volume of 1.2 ml was used. All samples were scanned from 25° C. to 90° C. at a rate of 90K/hour.

The results are presented in Table 1, below. Data for a lipase derived from *Candida antarctica* (Lipase B, obtained according to International Patent Application WO 88/02175) are shown for comparison, and it is seen that the lipase of the invention is surprisingly more thermostable in defiance of their homology.

TABLE 1

| | Thermal Denaturation Temperatures, $T_d$ | |
|---|---|---|
| pH | Hyphozyma lipase | Candida B lipase |
| 5 | 72.4 | 62.6 |
| 7 | 68.1 | 62.0 |
| 9 | 60.6 | 55.1 |
| 10 | 54.2 | 52.6 |

We claim:

1. A lipolytic enzyme characterized as:

(a) immunologically reactive with an antibody raised against a purified lipase derived from the strain Hyphozyma sp. LF132, CBS 648.91;

(b) derived from a strain belonging to the genus Hyphozyma; (c) having an optimal lipolytic activity in the temperature range of from 60° C. to 80° C. (when determined at pH 6.0); and (d) having an optimal lipolytic activity in the pH range of from 4.0 to 6.0 (when determined at 70° C.).

2. A lipolytic enzyme according to claim 1 comprising the following partial amino acid sequence:

Gly Ser Gly Xaa Xbb Lys Xaa Xaa Xaa Xaa Xaa Xaa Ser* Gln Gly Gly;

in which sequence Ser* represents the catalytically active serine, Xaa represents any of the naturally occurring amino acids, and Xbb represents a deletion or any of the naturally occurring amino acids except Asn.

3. A lipolytic enzyme according to claim 1 comprising the following partial amino acid sequence:

Gly Ser Gly Xaa Xbb Lys Xaa Pro Xaa Xaa Xaa Xaa Ser* Gln Gly Gly;

in which sequence Ser* represents the catalytically active serine, Xaa represents any of the naturally occurring amino acids, and Xbb represents a deletion or any of the naturally occurring amino acids except Asn.

4. A lipolytic enzyme according to claim 1 comprising the following partial amino acid sequence:

Gly Ser Gly Xaa Xbb Lys Xaa Pro Xaa Xaa Thr Xaa Ser* Gln Gly Gly;

in which sequence Ser* represents the catalytically active serine, Xaa represents any of the naturally occurring amino acids, and Xbb represents a deletion or any of the naturally occurring amino acids except Asn.

5. A lipolytic enzyme according to claim 1 comprising the following partial amino acid sequence:

Gly Ser Gly Xaa Xbb Lys Xaa Pro Xcc Xcc Thr Xaa Ser* Gln Gly Gly;

in which sequence Ser* represents the catalytically active serine, Xaa represents any of the naturally occurring amino acids, Xbb represents a deletion or any of the naturally occurring amino acids except Asn, and Xcc represents a hydrophobic amino acid.

6. A lipolytic enzyme according to claim 1 comprising the following partial amino acid sequence:

Gly Ser Gly Xaa Xbb Lys Xaa Pro Val Leu Thr Xaa Ser* Gln Gly Gly;

in which sequence Ser* represents the catalytically active serine, Xaa represents any of the naturally occurring amino acids, and Xbb represents a deletion or any of the naturally occurring amino acids except Asn.

7. A lipolytic enzyme according to claim 1 comprising the following partial amino acid sequence:

Gly Ser Gly Ser Xbb Lys Val Pro Val Leu Thr Xaa Ser* Gln Gly Gly;

in which sequence Ser* represents the catalytically active serine, Xaa represents any of the naturally occurring amino acids, and Xbb represents a deletion or any of the naturally occurring amino acids except Asn.

8. A lipolytic enzyme according to claim 1 having the amino acid sequence of SEQ ID NO: 3.

9. A process for obtaining a lipolytic enzyme according to claim 1, which process comprises cultivation of a lipase producing strain of the genus Hyphozyma in a suitable nutrient medium, containing carbon and nitrogen sources and inorganic salts, followed by recovery of the lipolytic enzyme.

10. A method for enzymatic pitch control comprising addition of a lipolytic enzyme according to claim 1, for hydrolysis of water-insoluble esters.

11. A method according to claim 10, in which a lipase dosage of 0.5–150 KLU/kg pulp, (dry substance) is employed.

12. A method according to claim 10, conducted at pH 3–7, at a temperature of 40°–90° C., at a reaction time of 0.5–5.0 hours, and a pulp consistency of 2–30% (w/w).

13. An immobilized lipase preparation obtained by immobilization of the lipolytic enzyme of claims 1.

14. An immobilized lipase preparation according to claim 13, wherein the lipase is immobilized on a particulate, macroporous weakly basic anion exchange resin.

15. An immobilized lipase preparation according to claim 13, wherein the lipase is immobilized on a particulate, porous non-ionic adsorbent resin.

16. An immobilized lipase preparation according to claim 13, wherein the lipase is immobilized on inorganic materials by adsorption, covalent coupling or precipitation.

17. An immobilized lipase preparation according to claim 13, wherein the lipase is immobilized on particles of naturally occurring organic materials.

18. The method of claim 11, wherein a lipase dosage of 20–75 KLU/kg pulp (dry substance) is employed.

19. The method of claim 11, wherein a lipase dosage of 5–20 KLU/kg pulp pulp (dry substance) is employed.

20. The method according to claim 12, conducted at pH 4–7, at a temperature of 50°–70° C., at a reaction time of 2.5–4 hours, and a pulp consistency of 3–8% (w/w).

21. The immobilized lipase preparation according to claim 14, wherein the anion exchange resin is selected from the group consisting of phenol-formaldehyde type resin or acrylic type resin.

22. The immobilized lipase preparation according to claim 15, wherein the non-ionic adsorbent resin is selected from the group consisting of a porous aliphatic olefinic polymer type resin or of an acrylic type resin.

23. The immobilized lipase preparation according to claim 16, wherein the inorganic materials is selected from the group consisting of zeolites, celites, porous glass beads, glass wool, aluminium oxides, kieselguhr, silicagel, and clay.

24. The immobilized lipase preparation according to claim 17, wherein the naturally occurring organic materials is selected from the group consisting of bone particles, chitin, chitosan, or agar.

* * * * *

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( x i ) SEQUENCE DESCRIPTION: SEQ ID NO:1:

```
Phe Thr Pro Phe Pro Thr Gly Ala Asp Pro Ala Phe Thr Gln Ser Gln
 1               5                  10                  15

Ala Thr Leu Asp Ala Gly Leu Thr
            20
```

( 2 ) INFORMATION FOR SEQ ID NO:2:

( i ) SEQUENCE CHARACTERISTICS:
( A ) LENGTH: 1026 base pairs
( B ) TYPE: nucleic acid
( C ) STRANDEDNESS: single
( D ) TOPOLOGY: linear ( x i ) SEQUENCE DESCRIPTION: SEQ ID NO:2:

```
ATGAAGCTCT CGTCGGCACT TGCCGGTCTG CTGGCCGTCG CCGCAGTTAC TGCCCTCCCT      60

GCCCCC TTT ACA CCC TTC CCC ACG GGC GCA GAC CCG GCC TTC ACT CAA       108
       Phe Thr Pro Phe Pro Thr Gly Ala Asp Pro Ala Phe Thr Gln
        1               5                  10

TCT CAG GCC ACT CTC GAT GCC GGC CTC ACC TGT CAG TCT GGC TCG CCT      156
Ser Gln Ala Thr Leu Asp Ala Gly Leu Thr Cys Gln Ser Gly Ser Pro
15                  20                  25                  30

TCG TCC CAG AAG AAC CCC ATC CTC CTC GTC CCG GGC ACC GGC AAC ACT      204
Ser Ser Gln Lys Asn Pro Ile Leu Leu Val Pro Gly Thr Gly Asn Thr
                35                  40                  45

GGC CCA CAG TCG TTC GAC TCG AAC TGG ATT CCG CTT TCC GCC CAG CTC      252
Gly Pro Gln Ser Phe Asp Ser Asn Trp Ile Pro Leu Ser Ala Gln Leu
            50                  55                  60

GGC TAC AGC CCT TGC TGG GTC TCT CCT CCG CCG TTC ATG CTC AAC GAC      300
Gly Tyr Ser Pro Cys Trp Val Ser Pro Pro Pro Phe Met Leu Asn Asp
        65                  70                  75

TCC CAG ATC AAC GCC GAG TAC ATT GTC AAT GCC ATC CAC ACC CTC TCC      348
Ser Gln Ile Asn Ala Glu Tyr Ile Val Asn Ala Ile His Thr Leu Ser
    80                  85                  90

TCG GGC TCC GGG TCC AAG GTT CCT GTT CTG ACC TGG AGT CAA GGT GGT      396
Ser Gly Ser Gly Ser Lys Val Pro Val Leu Thr Trp Ser Gln Gly Gly
95                 100                 105                 110

CTG GCG GCG CAA TGG GCG CTC ACT TTT TTC CCT AGC ACG CGC AAC AAG      444
Leu Ala Ala Gln Trp Ala Leu Thr Phe Phe Pro Ser Thr Arg Asn Lys
                115                 120                 125

GTC GAC CGC CTG ATG GCT TTT GCT CCT GAC TAC AAG GGC ACC GTT GAA      492
Val Asp Arg Leu Met Ala Phe Ala Pro Asp Tyr Lys Gly Thr Val Glu
            130                 135                 140

GCT GGT CTC CTC GAT GCG TTC GGC CTC AGC GCC CCG AGT GTC TGG CAG      540
Ala Gly Leu Leu Asp Ala Phe Gly Leu Ser Ala Pro Ser Val Trp Gln
        145                 150                 155

CAG ACC GCG CAG TCT GCC TTT GTC ACC GCG CTC GAC CAG GCC GGC GGA      588
Gln Thr Ala Gln Ser Ala Phe Val Thr Ala Leu Asp Gln Ala Gly Gly
    160                 165                 170
```

```
TTG AAC CAG ATC GTC CCC ACC ACC AAC CTC TAC TCG GCA ACC GAC GAG    636
Leu Asn Gln Ile Val Pro Thr Thr Asn Leu Tyr Ser Ala Thr Asp Glu
175                 180                 185                 190

GTC GTG CAG CCG CAG TTC GCC AAC GGG CCC CCG GAC TCT TCC TAC CTC    684
Val Val Gln Pro Gln Phe Ala Asn Gly Pro Pro Asp Ser Ser Tyr Leu
                195                 200                 205

TCT AAC GGC AAG AAC ATC CAG GCA CAG TCG ATC TGC GGC CCG CTC TTC    732
Ser Asn Gly Lys Asn Ile Gln Ala Gln Ser Ile Cys Gly Pro Leu Phe
            210                 215                 220

ATC ATC GGA CAC GCT GGT TCC CTG TAC TCG CAG TTC TCT TAC GTC GTC    780
Ile Ile Gly His Ala Gly Ser Leu Tyr Ser Gln Phe Ser Tyr Val Val
        225                 230                 235

GGC AAG AGT GCG CTC GCC TCG CCC ACC GGT CAG GCC CAG AGC AGC GAT    828
Gly Lys Ser Ala Leu Ala Ser Pro Thr Gly Gln Ala Gln Ser Ser Asp
    240                 245                 250

TAC AGC ATC AAG GAC TGC AAC CCG GCC CCT GCT AAC CCC CTC ACC GCC    876
Tyr Ser Ile Lys Asp Cys Asn Pro Ala Pro Ala Asn Pro Leu Thr Ala
255                 260                 265                 270

CAG CAG AAG CTC GAC TCT GCG GCG ATC ATC CTC GTC GCC GGC AAG AAT    924
Gln Gln Lys Leu Asp Ser Ala Ala Ile Ile Leu Val Ala Gly Lys Asn
                275                 280                 285

ATT GTC ACC GGT CCC AAG CAG AAC TGC GAA CCT GAC CTC ATG CCC TAC    972
Ile Val Thr Gly Pro Lys Gln Asn Cys Glu Pro Asp Leu Met Pro Tyr
            290                 295                 300

GCT CGC AAG TAC CGC ATC GGC AAG AAG ACC TGC TCG GGC GTC ATC ACT   1020
Ala Arg Lys Tyr Arg Ile Gly Lys Lys Thr Cys Ser Gly Val Ile Thr
        305                 310                 315

GGA TGA                                                           1026
Gly
```

( 2 ) INFORMATION FOR SEQ ID NO:3:

( i ) SEQUENCE CHARACTERISTICS:
( A ) LENGTH: 319 amino acids
( B ) TYPE: amino acid
( D ) TOPOLOGY: linear ( x i ) SEQUENCE DESCRIPTION: SEQ ID NO:3:

```
Phe Thr Pro Phe Pro Thr Gly Ala Asp Pro Ala Phe Thr Gln Ser Gln
  1               5                  10                  15

Ala Thr Leu Asp Ala Gly Leu Thr Cys Gln Ser Gly Ser Pro Ser Ser
             20                  25                  30

Gln Lys Asn Pro Ile Leu Leu Val Pro Gly Thr Gly Asn Thr Gly Pro
         35                  40                  45

Gln Ser Phe Asp Ser Asn Trp Ile Pro Leu Ser Ala Gln Leu Gly Tyr
     50                  55                  60

Ser Pro Cys Trp Val Ser Pro Pro Pro Phe Met Leu Asn Asp Ser Gln
 65                  70                  75                  80

Ile Asn Ala Glu Tyr Ile Val Asn Ala Ile His Thr Leu Ser Ser Gly
                 85                  90                  95

Ser Gly Ser Lys Val Pro Val Leu Thr Trp Ser Gln Gly Gly Leu Ala
            100                 105                 110

Ala Gln Trp Ala Leu Thr Phe Phe Pro Ser Thr Arg Asn Lys Val Asp
        115                 120                 125

Arg Leu Met Ala Phe Ala Pro Asp Tyr Lys Gly Thr Val Glu Ala Gly
    130                 135                 140

Leu Leu Asp Ala Phe Gly Leu Ser Ala Pro Ser Val Trp Gln Gln Thr
145                 150                 155                 160
```

Ala Gln Ser Ala Phe Val Thr Ala Leu Asp Gln Ala Gly Gly Leu Asn
165 170 175

Gln Ile Val Pro Thr Thr Asn Leu Tyr Ser Ala Thr Asp Glu Val Val
180 185 190

Gln Pro Gln Phe Ala Asn Gly Pro Pro Asp Ser Ser Tyr Leu Ser Asn
195 200 205

Gly Lys Asn Ile Gln Ala Gln Ser Ile Cys Gly Pro Leu Phe Ile Ile
210 215 220

Gly His Ala Gly Ser Leu Tyr Ser Gln Phe Ser Tyr Val Val Gly Lys
225 230 235 240

Ser Ala Leu Ala Ser Pro Thr Gly Gln Ala Gln Ser Ser Asp Tyr Ser
245 250 255

Ile Lys Asp Cys Asn Pro Ala Pro Ala Asn Pro Leu Thr Ala Gln Gln
260 265 270

Lys Leu Asp Ser Ala Ala Ile Ile Leu Val Ala Gly Lys Asn Ile Val
275 280 285

Thr Gly Pro Lys Gln Asn Cys Glu Pro Asp Leu Met Pro Tyr Ala Arg
290 295 300

Lys Tyr Arg Ile Gly Lys Lys Thr Cys Ser Gly Val Ile Thr Gly
305 310 315

( 2 ) INFORMATION FOR SEQ ID NO:4:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( x i ) SEQUENCE DESCRIPTION: SEQ ID NO:4:

Phe Thr Pro Phe Pro
1 5

( 2 ) INFORMATION FOR SEQ ID NO:5:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( x i ) SEQUENCE DESCRIPTION: SEQ ID NO:5:

Thr Gly Ala Asp Pro
1 5

( 2 ) INFORMATION FOR SEQ ID NO:6:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( x i ) SEQUENCE DESCRIPTION: SEQ ID NO:6:

Ala Phe Thr Gln Ser
1 5

( 2 ) INFORMATION FOR SEQ ID NO:7:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( x i ) SEQUENCE DESCRIPTION: SEQ ID NO:7:

Gln Ala Thr Leu Asp Ala Gly Leu Thr
1 5

( 2 ) INFORMATION FOR SEQ ID NO:8:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( x i ) SEQUENCE DESCRIPTION: SEQ ID NO:8:

Gly Ser Gly Ser Lys
1 5

( 2 ) INFORMATION FOR SEQ ID NO:9:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( x i ) SEQUENCE DESCRIPTION: SEQ ID NO:9:

Val Pro Val Leu Thr Trp Ser
1 5

( 2 ) INFORMATION FOR SEQ ID NO:10:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( x i ) SEQUENCE DESCRIPTION: SEQ ID NO:10:

Thr Trp Ser Gln Gly Gly Leu Ala Ala Gln
1 5 10

( 2 ) INFORMATION FOR SEQ ID NO:11:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( x i ) SEQUENCE DESCRIPTION: SEQ ID NO:11:

Ala Gln Gln Lys Leu Asp Ser Ala Ala Ile Ile Leu
1 5 10

( 2 ) INFORMATION FOR SEQ ID NO:12:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( x i ) SEQUENCE DESCRIPTION: SEQ ID NO:12:

Val Ala Gly Lys Asn Ile Val Thr Gly Pro Lys Gln
1 5 10

( 2 ) INFORMATION FOR SEQ ID NO:13:

( i ) SEQUENCE CHARACTERISTICS:

(A) LENGTH: 13 amino acids
(B) TYPE: amino acid
(C) STRANDEDNESS: single
(D) TOPOLOGY: linear (xi) SEQUENCE DESCRIPTION: SEQ ID NO:13:

Asn Cys Glu Pro Asp Leu Met Pro Tyr Ala Arg Lys Tyr
1 5 10

(2) INFORMATION FOR SEQ ID NO:14:

(i) SEQUENCE CHARACTERISTICS:
(A) LENGTH: 13 amino acids
(B) TYPE: amino acid
(C) STRANDEDNESS: single
(D) TOPOLOGY: linear (xi) SEQUENCE DESCRIPTION: SEQ ID NO:14:

Arg Ile Gly Lys Lys Thr Cys Ser Gly Val Ile Thr Gly
1 5 10

(2) INFORMATION FOR SEQ ID NO:15:

(i) SEQUENCE CHARACTERISTICS:
(A) LENGTH: 10 amino acids
(B) TYPE: amino acid
(C) STRANDEDNESS: single
(D) TOPOLOGY: linear (xi) SEQUENCE DESCRIPTION: SEQ ID NO:15:

Phe Thr Pro Phe Pro Thr Gly Ala Asp Pro
1 5 10

(2) INFORMATION FOR SEQ ID NO:16:

(i) SEQUENCE CHARACTERISTICS:
(A) LENGTH: 14 amino acids
(B) TYPE: amino acid
(C) STRANDEDNESS: single
(D) TOPOLOGY: linear (xi) SEQUENCE DESCRIPTION: SEQ ID NO:16:

Ala Phe Thr Gln Ser Gln Ala Thr Leu Asp Ala Gly Leu Thr
1 5 10

(2) INFORMATION FOR SEQ ID NO:17:

(i) SEQUENCE CHARACTERISTICS:
(A) LENGTH: 12 amino acids
(B) TYPE: amino acid
(C) STRANDEDNESS: single
(D) TOPOLOGY: linear (xi) SEQUENCE DESCRIPTION: SEQ ID NO:17:

Gly Ser Gly Ser Lys Val Pro Val Leu Thr Trp Ser
1 5 10

(2) INFORMATION FOR SEQ ID NO:18:

(i) SEQUENCE CHARACTERISTICS:
(A) LENGTH: 14 amino acids
(B) TYPE: amino acid
(C) STRANDEDNESS: single
(D) TOPOLOGY: linear (xi) SEQUENCE DESCRIPTION: SEQ ID NO:18:

Thr Trp Ser Gln Gly Gly Leu Ala Ala Gln Trp Ala Leu Thr
1 5 10

( 2 ) INFORMATION FOR SEQ ID NO:19:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( x i ) SEQUENCE DESCRIPTION: SEQ ID NO:19:

```
Ala Gln Gln Lys Leu Asp Ser Ala Ala Ile Ile Leu Val Ala Gly Lys
 1               5                  10                  15

Asn Ile Val Thr Gly Pro Lys Gln
                20
```

( 2 ) INFORMATION FOR SEQ ID NO:20:

( i ) SEQUENCE CHARACTERISTICS:
( A ) LENGTH: 26 amino acids
( B ) TYPE: amino acid
( C ) STRANDEDNESS: single
( D ) TOPOLOGY: linear ( x i ) SEQUENCE DESCRIPTION: SEQ ID NO:20:

```
Asn Cys Glu Pro Asp Leu Met Pro Tyr Ala Arg Lys Tyr Arg Ile Gly
 1               5                  10                  15

Lys Lys Thr Cys Ser Gly Val Ile Thr Gly
                20                  25
```

( 2 ) INFORMATION FOR SEQ ID NO:21:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( x i ) SEQUENCE DESCRIPTION: SEQ ID NO:21:

```
Gly Ser Gly Xaa Xaa Lys Xaa Xaa Xaa Xaa Xaa Xaa Ser Gln Gly Gly
 1               5                  10                  15
```

( 2 ) INFORMATION FOR SEQ ID NO:22:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( x i ) SEQUENCE DESCRIPTION: SEQ ID NO:22:

```
Gly Ser Gly Xaa Xaa Lys Xaa Pro Xaa Xaa Xaa Xaa Ser Gln Gly Gly
 1               5                  10                  15
```

( 2 ) INFORMATION FOR SEQ ID NO:23:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( x i ) SEQUENCE DESCRIPTION: SEQ ID NO:23:

```
Gly Ser Gly Xaa Xaa Lys Xaa Pro Xaa Xaa Thr Xaa Ser Gln Gly Gly
 1               5                  10                  15
```

( 2 ) INFORMATION FOR SEQ ID NO:24:

( i ) SEQUENCE CHARACTERISTICS:

(A) LENGTH: 16 amino acids
(B) TYPE: amino acid
(C) STRANDEDNESS: single
(D) TOPOLOGY: linear (xi) SEQUENCE DESCRIPTION: SEQ ID NO:24:

Gly Ser Gly Xaa Xaa Lys Xaa Pro Xaa Xaa Thr Xaa Ser Gln Gly Gly
1 5 10 15

(2) INFORMATION FOR SEQ ID NO:25:

(i) SEQUENCE CHARACTERISTICS:
(A) LENGTH: 16 amino acids
(B) TYPE: amino acid
(C) STRANDEDNESS: single
(D) TOPOLOGY: linear (xi) SEQUENCE DESCRIPTION: SEQ ID NO:25:

Gly Ser Gly Xaa Xaa Lys Xaa Pro Val Leu Thr Xaa Ser Gln Gly Gly
1 5 10 15

(2) INFORMATION FOR SEQ ID NO:26:

(i) SEQUENCE CHARACTERISTICS:
(A) LENGTH: 16 amino acids
(B) TYPE: amino acid
(C) STRANDEDNESS: single
(D) TOPOLOGY: linear (xi) SEQUENCE DESCRIPTION: SEQ ID NO:26:

Gly Ser Gly Ser Xaa Lys Val Pro Val Leu Thr Xaa Ser Gln Gly Gly
1 5 10 15

(2) INFORMATION FOR SEQ ID NO:27:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:27:

CGGGATCCTG CAACATGAAG CTCTCG 26

(2) INFORMATION FOR SEQ ID NO:28:

(i) SEQUENCE CHARACTERISTICS:
(A) LENGTH: 25 base pairs
(B) TYPE: nucleic acid
(C) STRANDEDNESS: single
(D) TOPOLOGY: linear (xi) SEQUENCE DESCRIPTION: SEQ ID NO:28:

CGGGATCCTC ATCCAGTGAT GACGC 25

(2) INFORMATION FOR SEQ ID NO:29:

(i) SEQUENCE CHARACTERISTICS:
(A) LENGTH: 21 amino acids
(B) TYPE: amino acid
(C) STRANDEDNESS: single
(D) TOPOLOGY: linear (xi) SEQUENCE DESCRIPTION: SEQ ID NO:29:

Phe Thr Pro Phe Pro Thr Gly Ala Asp Pro Ala Phe Thr Gln Ser Gln
1 5 10 15

Ala Thr Leu Asp Ala
20

-continued ( 2 ) INFORMATION FOR SEQ ID NO:30:

( i ) SEQUENCE CHARACTERISTICS:
( A ) LENGTH: 88 base pairs
( B ) TYPE: nucleic acid
( C ) STRANDEDNESS: single
( D ) TOPOLOGY: linear ( x i ) SEQUENCE DESCRIPTION: SEQ ID NO:30:

TTYACNCCNT TCCCNACNGG NGCNGACCCN GCNTTYACNC ARTCNCARGC NACNCTNGAC 60

GCNCGGAATT CTTCACNCCN TTCCCNAC 88

( 2 ) INFORMATION FOR SEQ ID NO:31:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( x i ) SEQUENCE DESCRIPTION: SEQ ID NO:31:

CGGGATCCGC GTCNAGNGTN GCYTG 25

( 2 ) INFORMATION FOR SEQ ID NO:32:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( x i ) SEQUENCE DESCRIPTION: SEQ ID NO:32:

ACGGGCGCAG ACCCGGCCTT CACTCAATCT C 31